United States Patent
Aronhime et al.

(10) Patent No.: US 7,122,681 B2
(45) Date of Patent: Oct. 17, 2006

(54) DESOLVATION PROCESS FOR THE PRODUCTION OF ATORVASTATIN HEMI-CALCIUM ESSENTIALLY FREE OF BOUND ORGANIC SOLVENT

(75) Inventors: Judith Aronhime, Rehovot (IL); Dalia Maidan-Hanoch, Kfar Yona (IL)

(73) Assignee: Teva Pharmaceutical Industries, Ltd., Petah Tiqva (IL)

( * ) Notice: Subject to any disclaimer, the term of this patent is extended or adjusted under 35 U.S.C. 154(b) by 0 days.

(21) Appl. No.: 10/370,424

(22) Filed: Feb. 19, 2003

(65) Prior Publication Data

US 2003/0216584 A1    Nov. 20, 2003

Related U.S. Application Data

(60) Provisional application No. 60/358,497, filed on Feb. 19, 2002.

(51) Int. Cl.
*C07D 207/335*    (2006.01)
(52) U.S. Cl. ..................................................... 548/537
(58) Field of Classification Search ................ 548/537; 514/423
See application file for complete search history.

(56) References Cited

U.S. PATENT DOCUMENTS

| | | | |
|---|---|---|---|
| 4,444,129 A | 4/1984 | Ladt | |
| 4,624,058 A | 11/1986 | Nakayasu et al. | |
| 4,681,893 A | 7/1987 | Roth | |
| 5,003,080 A | 3/1991 | Butler et al. | |
| 5,273,995 A | 12/1993 | Roth | |
| 5,298,627 A | 3/1994 | Butler et al. | |
| 5,969,156 A * | 10/1999 | Briggs et al. | 548/537 |
| 6,002,011 A | 12/1999 | Kato et al. | |
| 6,121,461 A * | 9/2000 | McKenzie | 548/530 |
| 6,605,636 B1 * | 8/2003 | Aronhime et al. | 514/423 |
| 6,605,729 B1 * | 8/2003 | Byrn et al. | 548/537 |
| 2002/0183378 A1 | 12/2002 | Aronhime et al. | |

FOREIGN PATENT DOCUMENTS

| | | |
|---|---|---|
| WO | WO 01/36384 | 5/2001 |
| WO | WO 01/44180 | 6/2001 |
| WO | WO 01/44181 | 6/2001 |
| WO | WO 02/043732 | 6/2002 |
| WO | WO 02/051804 | 7/2002 |
| WO | WO 02/059087 | 8/2002 |
| WO | WO 02/083637 | 10/2002 |
| WO | WO 02/083638 | 10/2002 |
| WO | WO 03/018547 | 3/2003 |
| WO | WO 03/070702 | 8/2003 |

* cited by examiner

*Primary Examiner*—Kamal A. Saeed
*Assistant Examiner*—Robert Shiao
(74) *Attorney, Agent, or Firm*—Kenyon & Kenyon LLP

(57) ABSTRACT

The present invention provides processes for removing organic solvent from crystals of atorvastatin hemi-calcium containing organic solvent. In one process, the organic solvent is displaced by vapor diffusion of water in a vessel maintained at elevated humidity. In a second process, the organic solvent is removed by fluidized bed drying. The present invention further provides atorvastatin hemi-calcium containing 1% or less organic solvent, which can be obtained from atorvastatin hemi-calcium that has been crystallized from an organic solvent-containing solution by practice of the processes of the invention.

37 Claims, 2 Drawing Sheets

US 7,122,681 B2

DESOLVATION PROCESS FOR THE PRODUCTION OF ATORVASTATIN HEMI-CALCIUM ESSENTIALLY FREE OF BOUND ORGANIC SOLVENT

CROSS REFERENCE TO RELATED APPLICATIONS

This application claims the benefit of U.S. provisional application No. 60/358,497, filed Feb. 19, 2002, which is incorporated by reference in its entirety.

FIELD OF THE INVENTION

The present invention relates to atorvastatin hemi-calcium and, more particularly, to removal of organic solvent from atorvastatin hemi-calcium solvates and mixed solvates that are obtained from known procedures that use mixtures of organic solvent and, optionally, water in the production of atorvastatin hemi-calcium and particular crystalline forms thereof.

BACKGROUND OF THE INVENTION

Crystallization is a convenient, effective technique for purifying organic compounds. Purification by crystallization generally involves dissolving an impure substance in a solvent, removing insoluble impurities by filtering the solution and then precipitating the desired compound from the solution. Most soluble impurities are excluded from the growing crystals as the compound crystallizes. Ideally, soluble impurities remain in solution and are separated from the crystals by separating the solvent and washing the crystals.

Bulk producers of small organic molecules like pharmaceuticals endeavor to develop optimal crystallization techniques and thereby avoid less convenient purification techniques like chromatography.

Molecules of the solvent used in the crystallization, which are usually low volume, low molecular weight species, sometimes become incorporated into crystals during crystallization. Large, highly branched molecules are especially prone to this phenomenon. Solid materials that are obtained when molecules of a compound (hereafter referred to as the "host" compound) co-crystallize with a solvent (or "guest") are called "solvates." In some solvates, molecules of the host compound and guest are incorporated into the crystal in a fixed stoichiometric ratio. Some workers in the field of solid state chemistry and materials science reserve the term "solvate" for crystals whose ratio of host to guest is non-variable. In this disclosure, the term is used in the more broad sense in which it is understood in these fields to refer to any crystalline substance in which solvent is incorporated into the crystal lattice. In some solvates, the ratio of host compound to the guest is variable. In such solvates, the amount of solvent incorporated into the crystal can depend upon the specific crystallization procedure used to obtain the material and the conditions under which the material is maintained, such as the temperature and pressure. Solvates may be mixed. In other words, a crystal may contain more than one type of guest molecule in the crystal lattice. It is particularly relevant to this invention that a crystal can be a solvate of water (known as a hydrate) and an organic solvent.

Turning to other relevant background information relating to this invention, atorvastatin is the trivial name of ([R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid. Atorvastatin is administered to patients at risk for heart disease to lower their low density lipoprotein levels. Atorvastatin can be safely administered orally as a hemi-calcium salt. The crystalline form of atorvastatin hemi-calcium that has been approved by United States Food and Drug Administration for medical use is a trihydrate.

Although there is a general interest among chemical manufacturers in doing chemical synthesis in water for environmental reasons, as yet, atorvastatin has not been synthesized and crystallized using only reactions conducted in water. When conducting a synthesis in purely aqueous solvents is impracticable, lower alcohol solvents are a favorable alternative because they are able to dissolve substances of low polarity that do not dissolve in water, their toxicity is low compared to many other organic solvents, their cost is low and their solubility in water is high, which allows continuous variation of the properties of the solvent system by varying the ratio of alcohol and water, which can occur over a wide range.

U.S. Pat. No. 5,273,995 describes a preparation of atorvastatin hemi-calcium in which the atorvastatin lactone is dissolved in a mixture of methanol and water. A little less than one equivalent of sodium hydroxide is added to the solution until the lactone has been opened as determined by high performance liquid chromatography (HPLC). Then, one equivalent or a slight excess of calcium chloride dihydrate ($CaCl_2 \cdot 2H_2O$) is added at elevated temperature. After completing the addition, atorvastatin hemi-calcium is obtained as a precipitate by cooling the solution.

U.S. Pat. No. 5,298,627 discloses another process for preparing atorvastatin hemi-calcium. First, atorvastatin sodium is produced from an N,N-diphenyl amide analog of atorvastatin without intermediate isolation of the lactone by treating the amide with sodium hydroxide in a mixture of methanol and water. Following workup, an aqueous layer containing methanol and atorvastatin sodium is obtained. An aqueous solution of calcium acetate ($Ca(OAc)_2$) is then added to this aqueous layer at room temperature and the hemi-calcium salt is then precipitated by cooling.

U.S. Pat. No. 5,969,156 discloses atorvastatin hemi-calcium crystalline Forms I, II and III. According to the three examples in the '156 patent, each of these crystalline forms is obtained from a solution of methanol and water. In Example 1, a solution of atorvastatin sodium in a methanol and water mixture is treated with a solution of calcium acetate hemihydrate in water. After seeding with a crystal of Form I, followed by heating to 51–57° C. for at least ten minutes and then cooling to 15–40° C., a precipitate is filtered off, washed with ethanol and water and dried at 60–70° C. under vacuum for 4 days to give "Form I atorvastatin" (presumably the hemi-calcium salt). In Example 2, Form II is said to result by suspending Form I in a mixture of methanol and water. In Example 3, Form IV is said to result by following generally the procedure for producing Form I but with certain variations. Form IV also is obtained by precipitation from a mixture of methanol and water.

U.S. Pat. No. 6,121,461 describes atorvastatin hemi-calcium Form III which, according to Example 3 of the '461 patent, can be prepared by exposing atorvastatin hemi-calcium Form II to 95% relative humidity for eleven days.

Commonly assigned, co-pending U.S. Patent Application Publication No. 2002/0183378 discloses crystalline Forms VI, VIII–XII of atorvastatin hemi-calcium. Some of the forms are accessible by contacting atorvastatin hemi-calcium with mixtures of water and a lower alcohol, while others are accessible by other processes. In particular, atorvastatin hemi-calcium Form VI is obtained from a mixture of acetone and water. Atorvastatin hemi-calcium Form VII is obtained by treating certain atorvastatin hemi-calcium polymorphs with ethanol, preferably absolute ethanol with a low water content.

Atorvastatin hemi-calcium Form VIII is prepared under controlled conditions by a variety of procedures, some of which involve contacting atorvastatin hemi-calcium with mixtures of lower alcohols and water. In our hands and on our instrumentation, Form VIII produced a powder X-ray diffraction pattern with peaks at 6.9, 9.3, 9.6, 16.3, 17.1, 19.2, 20.0, 21.6, 22.4, 23,9, 24.7, 25.6, and 26.5±0.2 degrees 2θ. Form VIII has a monoclinic unit cell with lattice dimensions: a=18.55–18.7 Å, b=5.52–5.53 Å, c=31.0–31.2 Å and angle β between the a and c axes of 97.5–99.5°. Form VIII produced a solid-state cross-polarized/magic angle spinning ("CP/MAS") $^{13}C$ nuclear magnetic resonance spectrum with resonances at shift positions of about 17.8, 20.0, 24.8, 25.2, 26.1, 40.3, 40.8, 41.5, 43.4, 44.1, 46.1, 70.8, 73.3, 114.1, 116.0, 119.5, 120.1, 121.8, 122.8, 126.6, 128.8, 129.2, 134.2, 135.1, 137.0, 138.3, 139.8, 159.8, 166.4, 178.8, 186.5 ppm. Obtaining CP/MAS $^{13}C$ NMR spectra with reproducible chemical shift positions can be difficult due to the need for an external standard. Chemical shift differences do not suffer from this problem. For atorvastatin hemi-calcium Form VIII, the shift differences between the lowest ppm resonance and the other resonances are: 2.2, 7.0, 7.4, 8.3, 22.5, 23.0, 23.7, 25.6, 26.3, 28.3, 53.0, 55.5, 96.3, 98.2, 101.7, 102.3, 104.0, 105.0, 108.8, 111.0, 111.4, 116.4, 117.3, 119.2, 120.5, 122.0, 142.0, 148.6, 161.0 and 168.7 ppm.

Further, according to the '378 publication, atorvastatin hemi-calcium Form IX can be obtained from heterogeneous mixtures of atorvastatin hemi-calcium and a diluent containing a lower alcohol and water. Atorvastatin hemi-calcium Form X can be prepared by reprecipitating certain crystalline forms of atorvastatin hemi-calcium from mixtures of ethanol and water. Atorvastatin hemi-calcium Form XI is obtained from a gel formed of atorvastatin hemi-calcium and isopropyl alcohol. Atorvastatin hemi-calcium Form XII is obtained after performing a functional group deprotection of an atorvastatin precursor in aqueous solvent.

Thus, it will be appreciated that mixtures of water and organic solvents, especially lower alcohols, are used extensively in the preparation of atorvastatin and its isolation as a hemi-calcium salt. When atorvastatin hemi-calcium is crystallized from mixtures of water and a lower alcohol as taught in the '995, '627 and '156 patents, and the '378 publication, it tends to form a mixed solvate with water and the lower alcohol. We have found that atorvastatin hemi-calcium obtained by crystallization from solvent systems containing lower alcohols like methanol, ethanol and butan-1-ol may contain from about 1% up to about 5% by weight of the alcohol in their crystal structure.

Some solvates can be desolvated by heating them and/or by placing them in a container that is maintained under positive vacuum. Depending on the host molecule and the particle size of the material, the ease of solvent release by heating and/or application of a vacuum may be facile, futile or somewhere in between. In many cases the desolvation requires heating to a temperature that produces an adverse effect on the quality of the product, both chemical and physical (which is the case with atorvastatin hemi-calcium). In addition, when the starting material is a mixed solvate and the desired product is a solvate of one of the solvent molecules initially present, heating and/or exposure to vacuum must selectively remove only the undesired solvent to be successful.

Where heating and reduced pressure fail, sometimes more exotic techniques will succeed at removing an undesirable solvent molecule from a mixed solvate. U.S. Pat. No. 6,080,759 describes a process for removing organic solvent from (−)-trans-4-(4'-fluorophenyl)-3-(3', 4'-methenedioxyphenoxymethyl)-piperidine (paroxetine hydrochloride) by displacement with water. In the examples of the '759 patent, paroxetine hydrochloride containing any of a variety of organic solvents was stirred in liquid water to reduce the amount of organic solvent. For instance, in Example 1, paroxetine hydrochloride containing 13% propan-2-ol was stirred in a beaker with water for twenty minutes and then separated and dried. This caused a recrystallization of the paroxetine hydrochloride in anhydrous Form A. The '759 technique of displacement with liquid water appears to have general applicability with paroxetine hydrochloride since the examples show that paroxetine can be desolvated of a wide variety of organic solvents by that technique. However, a technique that is general in the sense that it can be used to remove a variety of solvents from crystals of a host compound does not necessarily mean it is applicable to a different host compound. Indeed, in the study of crystals, the results obtained by manipulating a material are frequently counterintuitive. For example, U.S. Pat. No. 6,002,011 discloses a method for desolvating a benzimidazole alcohol solvate comprising forming a suspension of the solvate in water. The end product is not only substantially free of alcohol it is also substantially free of water. As another example, there is cortisone acetate which precipitates from polar solvents containing less than 1% water as a hydrate. However, increasing the amount of water above 1% favors the formation of anhydrous cortisone acetate. See Carless, J. E. et. al *J. Pharm. & Pharmacol.*1966, 18, 190S–197S.

Processes for freeing atorvastatin hemi-calcium solvates and mixed solvates of organic solvent and water of the organic component have now been discovered.

SUMMARY OF THE INVENTION

In a first aspect, the present invention provides a process for removing organic solvent from crystals of atorvastatin hemi-calcium containing organic solvent. In one process of the invention, the organic solvent is displaced with water by exposing the crystals to water vapor. In an especially preferred embodiment of this displacement process, atorvastatin hemi-calcium containing organic solvent is exposed to an ambient temperature atmosphere saturated with water until an organic solvent content of about 50 ppm or less is obtained. The present invention also provides a mild thermal process for removing organic solvent from crystals of atorvastatin hemi-calcium by fluidizing the crystals in a gas stream.

In a second aspect, the present invention provides atorvastatin hemi-calcium essentially free of organic solvent. By practicing the processes disclosed herein, atorvastatin hemi-calcium and hydrates thereof can be obtained with an organic solvent content of 1% or less, and about 0.5% or less, even about 50 ppm or less, when the preferred embodiments of the invention are followed.

In addition the invention provides pharmaceutical compositions and dosage forms containing atorvastatin hemi-calcium essentially free of organic solvent and methods of reducing the low density lipoprotein level of a patient by administering the compositions and dosage forms.

DETAILED DESCRIPTION OF THE PREFERRED EMBODIMENTS

Figure 1:
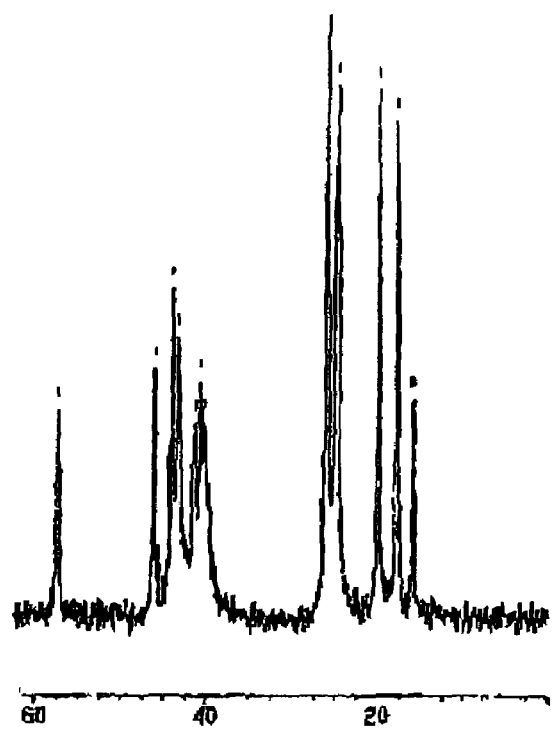
FIG. 1 shows the 0–60 ppm region of a solid-state CP/MAS $^{13}$C NMR spectrum of atorvastatin hemi-calcium Form VIII containing ethanol of solvation.

One object of the present invention is to provide a process for removing organic solvent from crystalline atorvastatin hemi-calcium. Another object of the present invention is to provide a process for selectively removing organic solvent from mixed solvates of crystalline atorvastatin hemi-calcium without causing significant decomposition of atorvastatin in the process. Such mixed solvates are produced by crystallization of atorvastatin hemi-calcium from mixtures of organic solvent and water. The objects of the invention have been realized by our discovery that contact of solvates and mixed solvates of atorvastatin hemi-calcium with water vapor under a sufficiently humid atmosphere substantially removes the organic solvent leaving an essentially pure hydrate of atorvastatin hemi-calcium.

Accordingly, the present invention provides a process for desolvating a crystalline atorvastatin hemi-calcium that contains organic solvent. The present invention also provides a process for selectively desolvating a mixed solvate of atorvastatin hemi-calcium. Such solvates are products of known processes for producing atorvastatin hemi-calcium and particular crystalline forms thereof as discussed previously in this disclosure. U.S. Pat. Nos. 5,273,995 and 5,298,627, which disclose processes for preparing atorvastatin and atorvastatin hemi-calcium are incorporated by reference in their entirety. U.S. Pat. Nos. 5,298,627 and 5,969,156, and U.S. Patent Publication No. 2002/0183378 which describe particular crystalline forms of atorvastatin hemi-calcium and processes for making them are also incorporated by reference in their entirety.

Organic solvents are molecules containing at least one carbon atom that are liquids at 25° C. Examples of organic solvents that can be removed from mixed solvates by the desolvation processes of the present invention include: alcohols, like, methanol, ethanol, propan-1-ol, propan-2-ol, butan-1-ol and 2-methyl propan-1-ol; ethers, like diethyl ether and methyl t-butyl ether; N,N-dialkyl amides, like N,N-dimethylformamide and N,N-dimethylacetamide; ketones, like acetone and butanone; dialkyl sulfoxides, like dimethyl sulfoxide; and the like.

In accordance with the inventive process, there is provided a starting material that is a solvate or mixed solvate of atorvastatin hemi-calcium in any crystalline polymorphic form known or yet to be discovered. Preferred starting materials are atorvastatin hemi-calcium Forms III–XII, with Forms VII and IX being especially preferred. The starting material is contacted with water vapor in a vessel whose interior space contains water vapor at a relative humidity higher than the relative humidity of the local atmosphere outside of the vessel. Contact is maintained for a period of time sufficient to effect removal of substantially all of the organic solvent from the starting material. The product so-formed is atorvastatin hemi-calcium essentially free of organic solvent or a hydrate thereof, which is then recovered from the vessel. Atorvastatin hemi-calcium can be recovered containing about 1% organic solvent or less, and about 0.5% or less, even about 50 ppm or less (ppm=$10^5$×(wt. %)), when the preferred embodiments of the invention are followed. The product can be used directly to prepare a pharmaceutical product or it can be subjected to further processing such as granulation, milling and the like.

In a preferred embodiment of the process, the mixed solvate of atorvastatin hemi-calcium is contacted with water vapor in a vessel whose interior space is maintained at about 60% to about 100% relative humidity. Relative humidity as a measure of atmospheric water content depends upon temperature. The process of the invention is preferably practiced at temperatures of from about 20 to about 100° C., more preferably of from about 40° C. to about 60° C. By practicing the invention within the preferred moisture and temperature ranges, levels of organic solvent down to a few ppm may be achieved in from as little as 6 hours' time up to several days' time. The final level of organic solvent will depend upon the organic solvent that must be removed and the relative humidity, temperature and contact time selected.

In an especially preferred embodiment of the displacement process, the mixed solvate is contacted with water vapor at 25±3° C., under a atmosphere saturated with water (100% RH) for from about 4 to about 18 days. An initial 2.5% ethanol impurity content can be reduced down to less than 50 ppm under these conditions.

Figure 2:
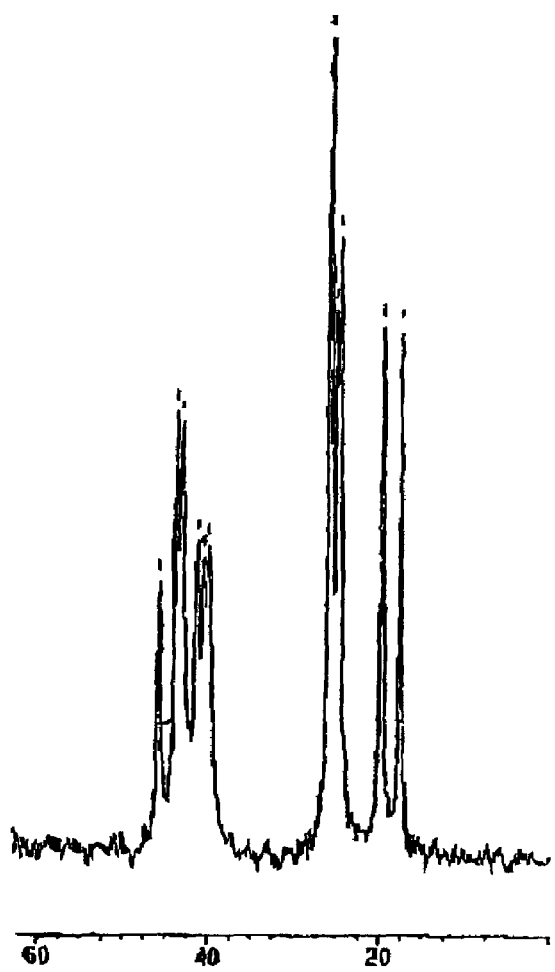
FIG. 2 shows the 0–60 ppm region of a solid-state CP/MAS $^{13}$C NMR spectrum of a sample of atorvastatin hemi-calcium Form VIII taken from the same production lot as the sample from which the spectrum in FIG. 1 was obtained. The sample was exposed to an atmosphere of 100% humidity for eighteen days before this spectrum was taken. Comparison of the 15.9 ppm and 57.4 ppm regions of this spectrum and FIG. 1 demonstrates the efficient removal of ethanol.

The efficacy of the process has been thoroughly evaluated by several analytical techniques. Example 1 employed Form VIII of atorvastatin hemi-calcium. FIG. 1 shows the relevant regions of a solid state $^{13}$C CP/MAS spectrum of the starting material. The resonance for the $CH_3$ $CH_2OH$ and $CH_3CH_2OH$ carbons of ethanol are observed at 15.9 and 57.4 ppm chemical shift, respectively. After maintaining the starting material under an atmosphere of 100% relative humidity at ambient temperature for 18 h., the ethanol content of the crystals had diminished beyond the limit of detection, as seen in FIG. 2.

In Examples 1–3, the amount of organic solvent remaining in the crystals after they have been subjected to the desolvation process was measured by gas chromatography using the head space technique (described below). In Examples 2 and 4, ethanol was not detectable in the product by gas chromatography. The limit of detection for this technique is adjudged to be about 50 ppm.

Figure 3:
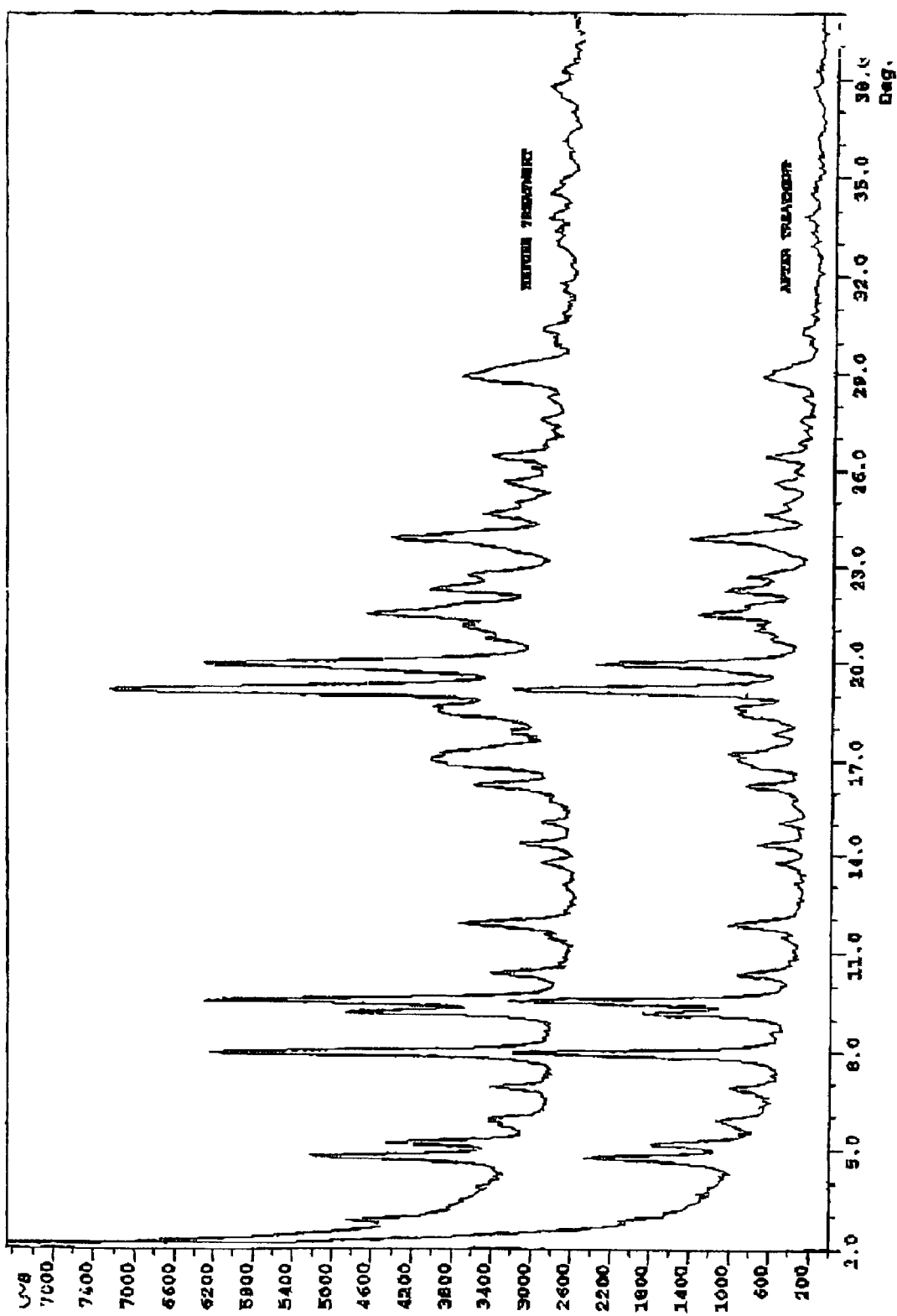
FIG. 3 shows powder X-ray diffraction patterns of atorvastatin hemi-calcium Form VIII that initially contained ethanol before and after being desolvated of ethanol in accordance with the process of the present invention.

Notably, desolvation of the crystals by our process does not necessarily cause a polymorphic transition in the crystals. For instance, in Example 3, atorvastatin hemi-calcium Form VIII containing 3 wt. % ethanol was desolvated. PXRD spectra of Form VIII were taken before and after desolvation. PXRD is like a fingerprint of a particular crystalline form. Essentially, no two are a like and therefore PXRD is highly probative of polymorphic identity compared to other techniques, such as infrared spectrometry. Referring to FIG. 3, comparison of the PXRD patterns of atorvastatin hemi-calcium Form VIII before and after desolvation clearly shows that the starting material and product have the same crystal structure. This result should be contrasted with the result achieved in Example 3 of U.S. Pat.

No. 6,121,461 where atorvastatin hemi-calcium Form II transformed into Form III upon exposure to 95% relative humidity. Comparison of FIG. 1 of the '461 patent with FIG. 2 of the '156 patent shows that Form II and Form III are not identical. Consequently, it is unexpected that contact of atorvastatin hemi-calcium Forms VIII, IX, or other forms with water vapor under our conditions did not induce a transformation to Form IV. Since, the present process has been shown to be effective without causing a polymorphic transformation using a representative selection of atorvastatin hemi-calcium polymorphs, the process is believed to be generally applicable to all crystalline forms of atorvastatin hemi-calcium, with Form II being an unique instance wherein the starting material undergoes a polymorphic transition under a humid atmosphere.

This vapor exchange process is convenient since it does not require subsequent removal of excess displacing solvent as, for instance, by filtration. Significantly, exchange of organic solvent with water does not occur when atorvastatin hemi-calcium containing organic solvent is contacted with liquid water. Even if it did occur, slurrying the crystals in water would necessitate subsequent manipulations like filtering and drying, some of which are always accompanied by some loss of material. In addition, whereas water used to slurry a compound that is destined to be taken internally by a patient must be scrupulously pure, ordinary tap water can be used to generate water vapor since evaporation serves to purify the water.

The object of removing organic solvent from a solvate or mixed solvate of atorvastatin hemi-calcium also has been realized by a thermal process that we discovered which uses milder conditions and requires less time than conventional thermal techniques. According to the thermal process of the present invention, an aqueous/organic mixed solvate of atorvastatin hemi-calcium is fluidized in a gas stream under conditions effective to liberate the organic solvent. The fluidized bed process is effective at selectively desolvating any aqueous/organic mixed solvate of atorvastatin hemi-calcium. Crystalline atorvastatin hemi-calcium like Form VIII and Form IX are especially preferred starting materials, though an aqueous/organic mixed solvate of any crystalline form is a suitable starting material.

Apparatuses for fluidized bed drying of granular materials are commercially available and have been described. See, for example, the descriptions of U.S. Pat. Nos. 4,444,129 and 4,624,058 which are herein incorporated by reference in their entirety. Fluidized bed dryers operate upon a common principle. The material to be dried is positioned on a perforated, conventionally flat or bowl-shaped support inside of a chamber. Hot gas is introduced into the chamber below the perforated support and is passed through the material to be dried through the perforations. The hot gas flowing through the bed of material "fluidizes" it, or in other words, keeps the particles in continuous motion balanced between gravity and the upward motion of hot gas. The hot gas is ultimately vented from the chamber at the top. Fluidized bed driers share the following operating parameters relevant to our process: gas inlet temperature and gas flux through the bed.

The inlet gas stream for thermal drying of atorvastatin hemi-calcium is preferably delivered below the crystal bed at a rate sufficient to fluidize the crystals, said flow rate being variable from apparatus-to-apparatus, but readily determinable by those skilled in the art. Preferably, the inlet gas temperature is from about 30° C. to about 70° C., more preferably, from about 40° C. to about 60° C. With effective fluidization and with gas stream temperatures in the preferred range, atorvastatin hemi-calcium containing about 3–5% ethanol can be desolvated to about 0.2% or less in about 6–8 hours. Atorvastatin hemi-calcium containing butan-1-ol requires more time, 24 hours or more being generally sufficient A second object of the invention is to provide atorvastatin hemi-calcium and hydrates thereof essentially free of organic solvent, other than Form I. Preferred hydrates are trihydrates containing 4.5±1 wt. % water and less than about 2 wt. % organic solvent, more preferably less than about 1 wt. % organic solvent and more preferably less than about 50 ppm organic solvent. The second object of the invention has been realized by discovery of the desolvation processes of the present invention which yield atorvastatin hemi-calcium hydrates with such a low organic solvent content.

Essentially pure atorvastatin hemi-calcium hydrates of the invention are useful for inhibiting the HMG-CoA reductase enzyme and reducing the low density lipoprotein level of mammalian patients, especially humans. For these purposes, they can be formulated into a variety of compositions for administration to humans and animals.

Pharmaceutical compositions of the present invention contain essentially pure atorvastatin hemi-calcium hydrates or mixtures thereof. In addition to the active ingredient(s), the pharmaceutical compositions of the present invention can contain one or more excipients. Excipients are added to the composition for a variety of purposes.

Diluents increase the bulk of a solid pharmaceutical composition and can make a pharmaceutical dosage form containing the composition easier for the patient and care giver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form like a tablet can include excipients whose functions include helping to bind the active ingredient and other excipients together after compression. Binders for solid pharmaceutical compositions include for example acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach can be increased by the addition of a disintegrant to the composition. Disintegrants include for example alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of non-compacted solid composition and improve the accuracy of dosing. Excipients that can function as glidants include for example colloidal silicon dioxide, magnesium trisilicate, powdered cellulose, starch, talc and tribasic calcium phosphate.

When a dosage form such as a tablet is made by compaction of a powdered composition, the composition is subjected to pressure from punches and a die. Some excipients and active ingredients have a tendency to adhere to the surfaces of the punches and die, which can cause the product to have pitting and other surface irregularities. A lubricant can be added to the composition to reduce adhesion and ease release of the product form the die. Lubricants include for example magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that can be included in the composition of the present invention include for example maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, the essentially pure atorvastatin hemi-calcium hydrate, and any other solid excipients are dissolved or suspended in a liquid carrier such as water, vegetable oil, polyethylene glycol, propylene glycol or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention can also contain a viscosity enhancing agent to improve the mouth-feel of the product and/or coat the lining of the gastrointestinal tract. Such agents include for example acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar can be added to improve the taste.

Preservatives and chelating agents such as alcohol, sodium benzoate, butylated hydroxy toluene, butylated hydroxyanisole and ethylenediamine tetraacetic acid can be added at levels safe for ingestion to improve storage stability.

A liquid composition according to the present invention can also contain a buffer such as guconic acid, lactic acid, citric acid or acetic acid, sodium guconate, sodium lactate, sodium citrate or sodium acetate.

Selection of excipients and the amounts to use can be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages can be conveniently presented in unit dosage form and prepared by any of the methods well-known in the pharmaceutical arts.

Dosage forms include solid dosage forms like tablets, powders, capsules, suppositories, sachets, troches and lozenges as well as liquid syrups, suspensions and elixirs.

A dosage form of the present invention is a capsule containing the composition, preferably a powdered or granulated solid composition of the invention, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filing can be prepared by wet granulation. In wet granulation some or all of the active ingredients and excipients in powder form are blended and then further mixed in the presence of a liquid, typically water, which causes the powders to clump up into granules. The granulate is screened and/or milled, dried and then screened and/or milled to the desired particle size. The granulate can then be tableted or other excipients can be added prior to tableting, such as a glidant and/or a lubricant.

A tableting composition can be prepared conventionally by dry blending. For instance, the blended composition of the actives and excipients can be compacted into a slug or a sheet and then comminuted into compacted granules. The compacted granules can be compressed subsequently into a tablet.

As an alternative to dry granulation, a blended composition can be compressed directly into a compacted dosage form using direct compression techniques. Direct compression produces a more uniform tablet without granules. Excipients that are particularly well-suited to direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, only they are not subjected to a final tableting step.

Capsules, tablets and lozenges and other unit dosage forms preferably contain a dosage level of about 10 to about 80 mg of essentially pure atorvastatin hemi-calcium hydrate. Other dosages may also be administered depending on the need.

Having thus described the present invention with reference to certain preferred embodiments, the present invention is further illustrated by the examples which follow. These examples are provided for illustrative purposes only and are not intended to limit in any way the invention which is defined by the claims which follow the examples.

EXAMPLES

Methodology

In the following examples, the organic solvent content of atorvastatin hemi-calcium crystals that have been subjected to the desolvation process of the invention was analyzed by gas chromatography using the head space technique. The sample was dissolved in dimethyl sulfoxide to give a 100 mg ml$^{-1}$ solution. Hewlett Packard HP-5890 and HP-6890 gas chromatographs were used. The chromatographs were equipped with megabore columns containing a medium polarity USP G43 stationary phase, or equivalent thereof, and a high polarity PEG stationary phase. Each had a FID detector and either a Combi Pal-CTC Analytics gas syringe system or a Hewlett Packard 7694 pressure/loop system.

The solid state $^{13}$C CP/MAS NMR spectra were obtained at 125.76 MHz, at ambient temperature on a Bruker DMX-500 digital FT NMR spectrometer equipped with a BL-4 CP/MAS probehead and a high resolution/high performance $^{1}$H preamplifier for solids. Samples were placed in 4 mm zirconia rotors and spun at 5.0 kHz, and the spinning side-bands were removed from the spectra using the SELTICS pulse sequence.

PXRD analysis was performed using conventional copper radiation by methods known in the art on a SCINTAG powder X-ray diffractometer model X'TRA equipped with a solid-state detector. Copper radiation of $\lambda=1.4518$ Å was used. The measurement range was 2–40 °2θ. The scan rate was 3° min$^{-1}$.

Example 1

Crystalline atorvastatin hemi-calcium Form VIII (500 mg) obtained by recrystallization from an ethanol and water mixture was used as the starting material. The starting material contained 2.5 wt. % ethanol. The starting material, was spread over the flat top surface of a 4 cm diameter dish. The dish was placed in a chamber at 100% relative humidity maintained at ambient temperature for 18 days. The atorvastatin hemi-calcium was collected and its ethanol content was measured by gas chromatography using the head space technique. The ethanol content was found to be less than 50 ppm.

Example 2

Crystalline atorvastatin hemi-calcium Form VIII (500 mg) obtained by recrystallization from an ethanol and water mixture was used as the starting material. The starting material contained 2.5 wt. % ethanol. The starting material, was spread over the flat top surface of a 4 cm diameter dish. The dish was placed in a chamber at 100% relative humidity maintained at ambient temperature for 4 days. The atorvastatin hemi-calcium was collected and its ethanol content was measured by gas chromatography using the head space technique. Ethanol was not detected.

Example 3

Atorvastatin hemi-calcium Form VIII (30 g) containing 3% ethanol, was mixed in a vacuum vessel equipped with a stirrer, in a humid atmosphere, at 40° C. for 5 hours. To humidify the atmosphere, water vapor was streamed through the vessel containing the atorvastatin hemi-calcium. The atorvastatin hemi-calcium Form VIII obtained contained 0.7% ethanol.

Example 4

Atorvastatin hemi-calcium Form VIII (18 g) containing about 50 wt. % water was suspended in a fluidized bed dryer for 7 hours at 60° C. to obtain atorvastatin hemi-calcium Form VIII with an undetectable level of residual ethanol as measured by gas chromatography using the head space technique.

Example 5

Atorvastatin hemi-calcium Form VIII (50 g) containing 3% ethanol was suspended in a fluidized bed dryer for 6 hours at 40° C. to obtain chemically pure atorvastatin hemi-calcium Form VIII with a residual ethanol content of 0.2% and water content of 3.1%.

Example 6

Atorvastatin hemi-calcium Form IX (12 g) containing about 4.5 wt. % butan-1-ol was suspended in a fluidized bed dryer for 24 h at 55° C. to obtain atorvastatin hemi-calcium Form IX containing about 1.5 wt. % butan-1-ol.

Example 7

Atorvastatin hemi-calcium Form IX (12 g) containing about 5.5 wt. % butan-1-ol was suspended in a fluidize bed dryer for 6 h at 50° C. to obtain atorvastatin hemi-calcium Form IX containing about 3.8 wt. % butan-1-ol.

Having thus described the invention with respect to certain preferred embodiments and further illustrated it with examples, those skilled in the art may come to appreciate substitutions and equivalents that albeit not expressly described are taught and inspired by this invention. Whereas such substitutions and equivalents do not depart from the spirit of the invention they are within its scope which is defined by the claims which follow.

What is claimed is:

1. A process for preparing crystalline forms of atorvastatin hemi-calcium essentially free of organic solvent, comprising:
   a) providing a solvate comprised of crystalline atorvastatin hemi-calcium and an organic solvent,
   b) contacting the solvate with water vapor in a vessel whose interior is maintained at an elevated humidity relative to the outside of the vessel, and
   c) recovering crystalline atorvastatin hemi-calcium essentially free of organic solvent.

2. The process of claim 1 wherein the solvate contains from about 1 to about 5 weight percent organic solvent.

3. The process of claim 1 wherein the solvate contains about 5 weight percent or less water.

4. The process of claim 2 wherein the organic solvent is selected from the group consisting of alcohols, ethers, N,N-dialkyl amides, ketones and, dialkyl sulfoxides.

5. The process of claim 4 wherein the organic solvent is selected from the group consisting of diethyl ether, methyl t-butyl ether; N,N-dimethylformamide, N,N-dimethylacetamide, acetone, butanone and dimethyl sulfoxide.

6. The process of claim 3 wherein the organic solvent is a $C_1$–$C_6$ lower alcohol.

7. The process of claim 6 wherein the $C_1$–$C_6$ lower alcohol is selected from the group consisting of methanol, ethanol, propan-1-ol, propan-2-ol, butan-1-ol and 2-methyl propan-1-ol.

8. The process of claim 1 wherein the water vapor is in an atmosphere of from about 60% to about 100% relative humidity.

9. The process of claim 2 wherein the atorvastatin hemi-calcium essentially free of organic solvent contains about 1 weight percent or less organic solvent.

10. The process of claim 9 wherein the atorvastatin hemi-calcium essentially free of organic solvent contains about 50 ppm or less organic solvent.

11. The process of claim 1 wherein the recovered crystalline atorvastatin hemi-calcium essentially free of organic solvent is an atorvastatin hemi-calcium trihydrate.

12. The process of claim 1 wherein the solvate of step a) is provided as a particular crystalline form and the crystalline atorvastatin hemi-calcium essentially free of organic solvent of step c) is the same crystalline form as the solvate of step a).

13. The process of claim 12 wherein the crystalline form of atorvastatin hemi-calcium is other than atorvastatin hemi-calcium Form II.

14. The process of claim 12 wherein the crystalline form is selected from the group consisting of atorvastatin hemi-calcium Forms I, III, IV, V, VI, VII, VIII, IX, X, XI, XII and mixtures thereof.

15. The process of claim 14 wherein the crystalline form is atorvastatin hemi-calcium Form VIII.

16. The process of claim 14 wherein the crystalline form is atorvastatin hemi-calcium Form IX.

17. The process of claim 1 wherein the solvate is a mixed solvate of the organic solvent and water and the crystalline atorvastatin hemi-calcium essentially free of organic solvent is a hydrate.

18. The process of claim 17 wherein the mixed solvate is provided as a particular crystalline form and the crystalline atorvastatin hemi-calcium essentially free of organic solvent is the same crystalline form as the mixed solvate.

19. The process of claim 18 wherein the crystalline form of atorvastatin hemi-calcium is other than atorvastatin hemi-calcium Form II.

20. The process of claim 18 wherein the crystalline form is selected from the group consisting of atorvastatin hemi-calcium Forms I, III, IV, V, VI, VII, VIII, IX, X, XI, XII and mixtures thereof.

21. The process of claim 20 wherein the crystalline form is atorvastatin hemi-calcium Form VIII.

22. The process of claim 20 wherein the crystalline form is atorvastatin hemi-calcium Form IX.

23. The process of claim 17 wherein the mixed solvate contains more water than organic solvent on a weight basis.

24. The process of claim 23 wherein the mixed solvate contains from about 1 to about 4 weight percent organic solvent.

25. The process of claim 17 wherein the mixed solvate contains 5 weight percent or less water.

26. The process of claim 17 wherein the organic solvent is selected from the group consisting of alcohols, ethers, N,N-dialkyl amides, ketones and, dialkyl sulfoxides.

27. The process of claim 26 wherein the organic solvent is selected from the group consisting of diethyl ether, methyl t-butyl ether; N,N-dimethylformamide, N,N-dimethylacetamide, acetone, butanone and dimethyl sulfoxide.

28. The process of claim 17 wherein the organic solvent is a $C_1$–$C_6$ lower alcohol.

29. The process of claim 28 wherein the organic solvent is selected from the group consisting of methanol, ethanol, propan-1-ol, propan-2-ol, butan-1-ol and 2-methyl propan-1-ol.

30. The process of claim 17 wherein the elevated humidity is from about 40% to about 100% relative humidity.

31. The process of claim 30 wherein the vessel is maintained at from about 20° C. to about 100° C. during contacting.

32. The process of claim 31 wherein recovery occurs from about 6 hours to about 20 days after contacting begins.

33. The process of claim 17 wherein the hydrate of atorvastatin hemi-calcium essentially free of organic solvent contains about one weight percent or less organic solvent.

34. The process of claim 33 wherein the hydrate of atorvastatin hemi-calcium essentially free of organic solvent contains about 50 ppm or less organic solvent on a weight basis.

35. The process of claim 17 wherein the hydrate of atorvastatin hemi-calcium essentially free of organic solvent is atorvastatin hemi-calcium trihydrate.

36. The process of claim 8 wherein the vessel is maintained at from about 20° C. to about 100° C. during contacting.

37. The process of claim 8 wherein the water vapor is in an atmosphere of about 100% relative humidity.

* * * * *